United States Patent
Hurtel et al.

(10) Patent No.: US 6,437,173 B1
(45) Date of Patent: Aug. 20, 2002

(54) PROCESS FOR THE CONTINUOUS MANUFACTURING OF DIALKYLAMINOALKYL (METH) ACRYLATES HAVING A CRITICAL ORDER OF STEPS

(75) Inventors: Patrice Hurtel, Bernay; Charles Hazan, Paris; Norbert Richard, Le Montat, all of (FR)

(73) Assignee: Elf Atochem S.A. (FR)

( * ) Notice: Subject to any disclaimer, the term of this patent is extended or adjusted under 35 U.S.C. 154(b) by 0 days.

(21) Appl. No.: 09/295,332

(22) Filed: Apr. 21, 1999

(30) Foreign Application Priority Data

Apr. 21, 1998 (FR) .............................. 98/04964

(51) Int. Cl.⁷ .............................................. C07C 67/03
(52) U.S. Cl. ....................................... 560/217; 562/222
(58) Field of Search .................... 560/222, 217

(56) References Cited
U.S. PATENT DOCUMENTS 4,851,568 A   7/1989   Hurtel et al.

OTHER PUBLICATIONS

Abstract of JP 03 112949.

Abstract of BR 8,701,337.

Primary Examiner—Johann Richter
Assistant Examiner—Robert W. Deemie
(74) Attorney, Agent, or Firm—Millen, White, Zelano & Branigan, P.C.

(57) ABSTRACT

The present invention relates to the manufacture of a dialkylaminoalkyl (meth)acrylate by transesterification of methyl or ethyl (meth)acrylate with an amino alcohol. The transesterification catalyst is chosen from tetrabutyl, tetraethyl and tetra(2-ethylhexyl) titanates. The reaction is carried out in a stirred reactor at 90–120° C., after which the crude reaction mixture is sent to a tailing column (C1), the flow from the top of this column is sent to a topping column (C2) and the flow from the bottom of this column si then sent to a final rectification column (C3). A dialkylaminoalkyl (meth) acrylate of high purity is obtained in this way.

16 Claims, 1 Drawing Sheet

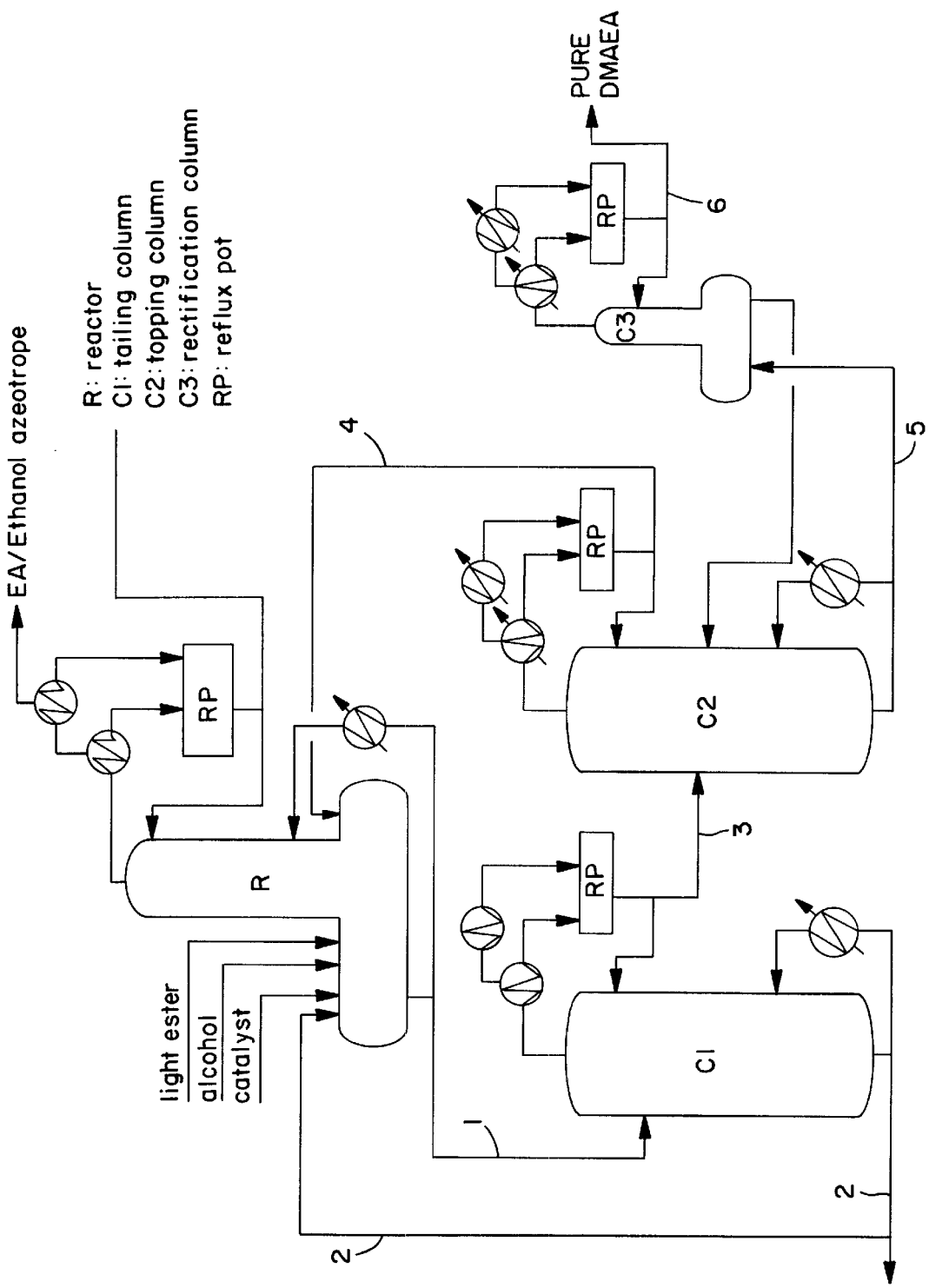

PROCESS FOR THE CONTINUOUS MANUFACTURING OF DIALKYLAMINOALKYL (METH) ACRYLATES HAVING A CRITICAL ORDER OF STEPS

BACKGROUND OF THE INVENTION

The present invention relates to a process for the continuous manufacture of a dialkylaminoalkyl (meth)acrylate of formula (I):

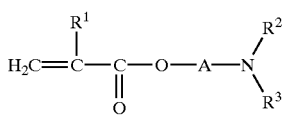

in which:
$R^1$ is a hydrogen atom or a methyl radical;
A is a linear or branched $C_1$–$C_5$ alkylene radical; and
$R^2$ and $R^3$, which may be identical to or different from each other, each represent a $C_1$–$C_4$ alkyl radical,
by reaction in a stirred reactor between a compound of formula (II):

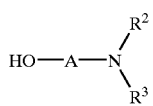

in which A, $R^2$ and $R^3$ have the same meanings as above, and a compound of formula (III):

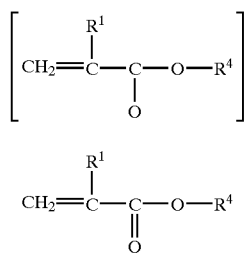

in which:
$R^1$ is as defined above; and
$R^4$ is a linear alkyl group containing 1 or 2 carbon atoms, in the presence of a tetraalkyl titanate as a transesterification catalyst and in the presence of at least one polymerization inhibitor, the compound (III)/$R^4$OH azeotropic mixture being removed continuously during the reaction.

French patent No. 1,544,542 describes the preparation of dimethylaminoethyl acrylate from $H_2C$=CHCOOCH $(CH_3)_2$ or from $H_2C$=CHCOOCH$_2$CH(CH$_3)_2$ and from alcohols in the presence of a catalyst such as n-propyl, isopropyl or isobutyl titanate and polybutyl titanate. This process has the drawback that the transesterification of titanates either with the light alcohol released during the reaction, or with the starting alcohol, causes the appearance of impurities in the reaction mixture and complicates the purification of the acrylic ester prepared.

In an attempt to overcome this problem, French patent No. 2,617,840 proposes a process for manufacturing compounds of formula (I) above, according to which ethyl (meth)acrylate is reacted, in the presence of at least one polymerization inhibitor, at 20–120° C. and at a pressure equal to or less than atmospheric pressure, with an amino alcohol of formula (II) above in an ethyl (meth)acrylate/amino alcohol (II) molar ratio of between 1.5 and 5, in the presence of tetraethyl titanate, the ethyl (meth)-acrylate/ethanol azeotropic mixture being removed during the reaction, and the compound (I) obtained being separated out at the end of the reaction.

The problem currently arising is that of the production on an industrial scale, continuously and with high purity, of these compounds (I). Thus, for example, it is sought to obtain dimethylaminoethyl acrylate (DMAEA) containing less than 100 ppm of ethyl acrylate (EA) and less than 300 ppm of dimethylaminoethanol (DMAE).

European patent EP-B-0,160,427 describes a process for manufacturing DMAEA which can be represented schematically as follows:

(1) Preparation of the Catalyst

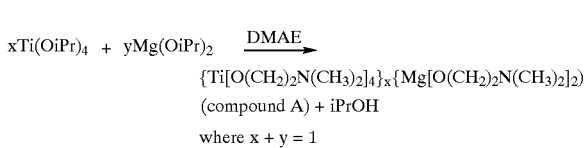

(2) Synthesis of DMAEA by Exchange Reaction in the Presence of Methyl Acrylate

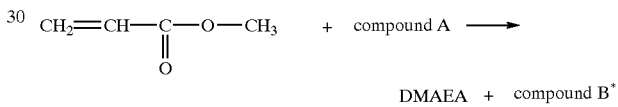

compound B=compound A partially modified with CH$_3$OH ligands from the methyl acrylate.

Compound B is then separated from the crude reaction mixture by a flash distillation, and the light phase obtained from this operation, containing the DMAEA and the excess unreacted methyl acrylate, is distilled to isolate the pure DMAEA.

(3) Regeneration of Compound A

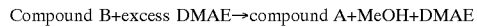

A flash distillation makes it possible to isolate compound A from the light phase containing the methanol and the DMAE. Compound A is recycled into step (2) and the light phase is distilled to separate the methanol from the DMAE, which is recycled into step (3).

This process, indicated in the abovementioned patent as being able to be carried out continuously, although no temperature or pressure data were provided for the abovementioned distillations, is still relatively complicated.

Brazilian patent No. PI 87/01337 describes a transesterification of a light (methyl) acrylate (without specifying that the heavy alcohol can be DMAE) continuously, according to which the reactor used is a tubular reactor in combination with an evaporator. The flow of vapour obtained in the evaporator is sent to a distillation column in order to separate:
  the light acrylate/light alcohol (methanol) azeotrope at the top; and
  the heavy acrylate and the heavy alcohol, with a small amount of light acrylate, at the bottom.

This last flow is sent to a purification column, from which a stream rich in heavy alcohol leaves, at the top, and is recycled into the reactor (topping). The titanate (catalyst) and the heavy acrylate leave at the bottom of this column. This flow is sent to a final column, from which the pure heavy acrylate leaves at the top and the catalyst leaves at the bottom.

This process does not make it possible, in the case of the synthesis of DMAEA, to obtain a product which satisfies the abovementioned specifications.

Brazilian patent No. PI 87/01338 describes, for the same reaction (still without specifically mentioning the amino alcohols as heavy alcohols), the use of a distillation column fed in the top part with the heavy alcohol and the catalyst (example: butyl titanate), and in the bottom part with the light acrylate. The flow leaving at the top is rich in light alcohol and contains light acrylate and heavy alcohol; the light acrylate is separated out and recycled into the column. The flow leaving at the bottom is rich in heavy acrylate (2-ethylhexyl acrylate in the example) and contains heavy alcohol and light acrylate.

SUMMARY OF THE INVENTION

It has now been discovered that by first carrying out a tailing operation (removal of the catalyst and the heavy products), followed by a topping operation and a final rectification, on a crude reaction mixture from the transesterification of alkyl (meth)acrylate (III) as defined above with an amino alcohol (II) as defined above, it is possible industrially to obtain a (meth)acrylate (I) of high purity.

A subject of the present invention is thus, firstly, a process for the continuous manufacture of a (meth)acrylate (I), as defined above, characterized in that the transesterification catalyst is chosen from tetrabutyl, tetraethyl and tetra(2-ethylhexyl) titanates, and in that the reaction is carried out in the stirred reactor at a temperature of 90–120° C., after which the following steps are carried out:

the crude reaction mixture comprising the desired heavy ester (I) with, as light products, compound (II) and the unreacted light ester (III), and, as heavy products, the catalyst, the polymerization inhibitor(s) and heavy reaction products, is sent to a first distillation column (C1) under reduced pressure, and a distillation is carried out in the said first column (C1), which makes it possible to obtain:

at the top, a flow composed essentially of the heavy ester (I) and the light products, containing a small fraction of heavy products, but free or substantially free of catalyst; and at the bottom, a flow of heavy products with a small fraction of heavy ester (I) and the catalyst; after which the flow from the top of the first distillation column (C1) is sent to a second distillation column (C2) under reduced pressure, in which a distillation is carried out which makes it possible to obtain:

at the top, a flow of the light products with a small fraction of heavy ester (I); and at the bottom, the heavy ester (I) containing traces of light products, heavy reaction products and the polymerization inhibitor(s); and the flow from the bottom of the second distillation column (C2) is sent to a third distillation column (C3) under reduced pressure, in which a rectification is carried out which makes it possible to obtain:

at the top, the desired heavy ester (I); and at the bottom, essentially the polymerization inhibitor (s).

In general, the reaction is carried out in the reactor (R) in an alkyl (meth)acrylate (III)/amino alcohol (II) molar ratio of between 1.1 and 3, preferably between 1.7 and 2.2; the catalyst is used in a proportion of from $10^{-4}$ to $10^{-2}$ mol per mole of amino alcohol (II), preferably in a proportion of from $1\times10^{-3}$ to $8\times10^{-3}$ mol per mole of amino alcohol (II); the reaction is carried out in the reactor (R) at a pressure of between 650 millibar and atmospheric pressure.

Moreover, the stabilizer(s) is (are) chosen from phenothiazine, tert-butylcatechol, hydroquinone methyl ether, hydroquinone and mixtures thereof in all proportions, and it is (they are) used in a proportion of 100–5000 ppm relative to the reaction feedstock. A stabilizer such as phenothiazine can also be added into the column (C2).

As examples of amino alcohols (II), mention may be made of dimethylaminoethanol (DMAE), dimethylaminopropanol and diethylaminoethanol.

In accordance with preferred characteristics of the process according to the present invention, the first distillation column (C1) is run at a pressure of $3.73\times10^3$–$1.04\times10^4$ Pa (28–78 mm Hg) at a temperature at the bottom of 100–115° C.;

the second distillation column (C2) is run at a pressure of $9.33\times10^3$–$1.07\times10^4$ Pa (70–80 mm Hg) at a temperature at the bottom of 110–125° C.;

the flow from the bottom of column (C1) is optionally recycled into the reactor (R) after purification by passage through a film evaporator, as is the flow from the top of column (C2); and the rectification column (C3) is run at a pressure of $3.73\times10^3$–$70.7\times10^3$ Pa (28–53 mm Hg) at 82–94° C.

The examples which follow illustrate the present invention without, however, limiting its scope. The results of various operations have been collated in each of them. The percentages are given on a weight basis.

BRIEF DESCRIPTION OF THE DRAWINGS

Columns (C1), (C2) and (C3) were used, which are installed according to the scheme in the single FIGURE in the attached drawing; the reaction (R) and these three columns each have a reflux pot (RP) mounted on top of them. The columns were run under the Pressure and temperature conditions indicated above. The reference numerals in Example 1 refer to the drawing.

Example 1

Synthesis of DMAEA

Starting with a crude reaction mixture 1, obtained by continuous reaction of DMAE with ethyl acrylate in the presence of phenothiazine as polymerization inhibitor and ethyl titanate as catalyst, giving a titre, per 100% by weight, of:

DMEA . . . 50–55%

Ethyl acrylate . . . 20–30%

DMEA . . . 15–25%

Heavy reaction products, catalyst and phenothiazine . . . 1.2–2.5%

The tailing column (C1) is fed continuously.

After purification by passing it through a film evaporator, the tail fraction (2) from this column (C1) is sent into the reaction.

A flow (3) free of catalyst is recovered at the top of this column (C1), with a titre, by weight, of:

DMEA . . . 50–55%
Ethyl acrylate . . . 20–30%
DMEA . . . 15–20%
Heavy reaction products, and phenothiazine . . . 1–5%
This flow 3, stabilized with phenothiazine, is sent to the topping column (C2).
The head fraction (4) from this column (C2) has the following composition (% by weight):
DMAEA . . . 5–10%
Ethyl acrylate . . . 40–60%
DMAE . . . 25–45%
It is recycled into the reaction.
The tail fraction (5) from this column (C2) has the following composition, by weight:
DMAEA . . . 99.8–99.9%
Ethyl acrylate . . . 0–10 ppm
DMAE . . . 50–150 ppm
Phenothiazine . . . 500–600 ppm
It is sent to column (C3), which makes it possible to obtain at the top (6) pure DMAEA with a composition (by weight) of:
DMAEA . . . 99.8%
Ethyl acrylate . . . <10 ppm
DMAE . . . 120–150 ppm
Phenothiazine . . . <1 ppm Example 2 (Comparative)

The same operations carried out with a topping operation followed by a tailing operation lead to a DMAEA product with a titre, by weight, of:
DMAEA . . . 99.5%
EA . . . 500 ppm
DMAE . . . 1000–2000 ppm From the above examples, it is seen that the order of steps is unexpectedly critical for obtaining a product having less than 100 ppm ethyl acrylate (EA) and less than 300 ppm dimethylaminoethanol (DMAE). Thus, it is contemplated that the purification procedure of this invention will be useful for other systems involving different catalysts and operating conditions for the production of DMAEA.

The film evaporator used to purify the recycle stream can be any conventional evaporator known for the ability to handle heat-sensitive materials, e.g., agitated thin film evaporators, falling film evaporator etc.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above, and of corresponding French application 98 04964, filed Apr. 21, 1998, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the continuous manufacture of a dialkylaminoalkyl (meth)acrylate of formula (I):

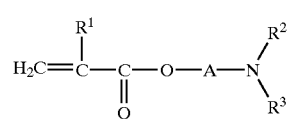

in which:
$R^1$ is a hydrogen atom or a methyl radical;
A is a linear or branched $C_1$–$C_5$ alkylene radical; and
$R^2$ and $R^3$, which may be identical to or different from each other, each represent a $C_1$–$C_4$ alkyl radical, by reaction in a stirred reactor R between a compound of formula (II):

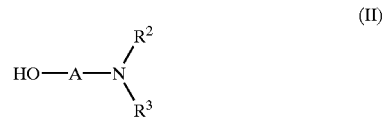

in which A, $R^2$ and $R^3$ have the same meanings as above, and a compound of the formula (III):

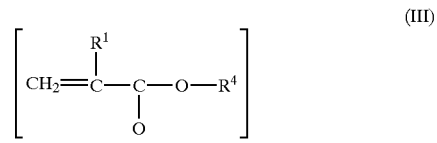

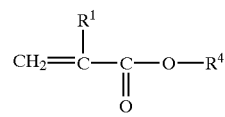

in which:
$R^1$ is as defined above; and
$R^4$ is a linear alkyl group containing 1 or 2 carbon atoms,
in the presence of a tetraalkyl titanate as a transesterification catalyst and in the presence of at least one polymerization inhibitor, the compound (III)/$R^4$OH azeotropic mixture being removed continuously during the reaction,
wherein the transesterification catalyst is a tetrabutyl, tetraethyl or tetra(2-ethylhexyl) titanate, the reaction being carried out in the stirred reactor at a temperature of 90–120° C., and subsequently;
distilling a crude reaction mixture comprising desired heavy ester (I) with, as light products, compound (II) and unreacted light ester (III), and, as heavy products, catalyst, polymerization inhibitor(s) and heavy reaction products, in a first distillation column (C1) under reduced pressure, to obtain:
at the top, a flow composed essentially of the heavy ester (I) and the light products, containing a small fraction of heavy products, but free of catalyst; and
at the bottom, a flow of heavy products with a small fraction of heavy ester (I) and the catalyst;
distilling the flow from the top of the first distillation column (C1) in a second distillation column (C2) under reduced pressure, to obtain;
at the top, a flow of the light products with a small fraction of heavy ester (I); and
at the bottom, the heavy ester (I) containing traces of light products, heavy reaction products and polymerization inhibitor(s); and distilling the flow from the bottom of the second distillation column (C2) in a third distillation column (C3) under reduced pressure, in which a rectification is carried out to obtain:
at the top, desired heavy ester (I); and
at the bottom, essentially polymerization inhibitor(s).

2. A process according to claim 1, wherein the reaction is carried out in a reactor (R) in an alkyl (meth)acrylate (III)/amino alcohol (II) molar ratio of 1.1 to 3.

3. A process according to claim 1, wherein the catalyst is used in a proportion of $10^{-4}$ to $10^{-2}$ mol per mole of amino alcohol (II).

4. A process according to claim 1, wherein the reaction is carried out in reactor (R) at a pressure of 650 millibar to atmospheric pressure.

5. A process according to claim 1, wherein the polymerization inhibitors(s) is phenothiazine, tert-butylcatechol, hydroquinone methyl ether, hydroquinone or mixtures thereof in all proportions, the polymerization inhibitor(s) being used in a proportion of 100–5000 ppm relative to the reaction feedback.

6. A process according to claim 1, wherein dimethylaminoethanol, dimethylaminopropanol or diethylaminoethanol is used as amino alcohol (II).

7. A process according to claim 1, wherein distillation column (C1) is run at a pressure of $3.73 \times 10^3 – 1.04 \times 10^4$ Pa at a temperature at the bottom of 100–115° C.

8. A process according to claim 1, wherein second distillation column (C2) is run at a pressure of $9.33 \times 10^3 – 1.7 \times 10^4$ Pa at a temperature at the bottom of 110–125° C.

9. A process according to claim 1, wherein flow from the bottom of column (C1) is recycled into reactor (R) after purification by passage through a film evaporator, along with flow from the top of column (C2).

10. A process according to claim 1, wherein rectification column (C3) is run at a pressure of $3.73 \times 10^3 – 70.7 \times 10^3$ Pa at 82–94° C.

11. A process according to claim 7, wherein the second distillation column (C2) is run at a pressure of $9.33 \times 10^3 – 1.7 \times 10^4$ Pa at a temperature at the bottom of 100–125° C.

12. A process according to claim 11, wherein the rectification column (C3) is run at a pressure of $3.73 \times 10^{-3} – 70.7 \times 10^3$ Pa at 82–94° C.

13. A process according to claim 12, wherein flow from the bottom of column (C1) is recycled into reactor (R) after purification by passage through a film evaporator, along with flow from the top of column (C2).

14. A process for the continuous manufacture of a dialkylaminoalkyl (meth)acrylate of formula (I):

$$H_2C=C(R^1)-C(=O)-O-A-N(R^2)(R^3) \quad (I)$$

in which:
$R^1$ is a hydrogen atom or a methyl radical;
A is a linear or branched $C_1$–$C_5$ alkylene radical; and
$R^2$ and $R^3$, which may be identical to or different from each other,
each represent a $C_1$–$C_4$ alkyl radical,
by reaction in a stirred reactor between a compound of formula (II):

$$HO-A-N(R^2)(R^3) \quad (II)$$

in which A, $R^2$ and $R^3$ have the same meanings as above, and a compound of formula (III):

$$CH_2=C(R^1)-C(=O)-O-R^4 \quad (III)$$

in which:
$R^1$ is as defined above; and
$R^4$ is a linear alkyl group containing 1 or 2 carbon atoms,
in the presence of a transesterification catalyst and in the presence of at least one polymerization inhibitor, and
Passing the crude reaction mixture comprising the desired heavy ester (I) with, as light products, compound (II), and the unreacted light ester (III), and, as heavy products, the catalyst, the polymerization inhibitor(s) and heavy reaction products, to a first distillation column (C1) under reduced pressure, and
at the top, a flow composed essentially of the heavy ester (I) and the light products, containing a minor fraction of heavy products, but substantially free of catalyst; and
at the bottom, a flow of heavy products the catalyst and a minor fraction of heavy ester (I); and
Passing the flow from the top of the first distillation column (C1) to a second distillation column (C2) under reduced pressure, to obtain:
at the top, a flow of the light products with a minor fraction of heavy ester (I); and
at the bottom, the heavy ester (I) containing traces of light products, heavy reaction products and the polymerization inhibitor(s); and
Passing the flow from the bottom of the second distillation column (C2) to a third distillation column (C3) under reduced pressure, to obtain:
at the top, the desired purified heavy ester (I); and
at the bottom, a flow of essentially the polymerization inhibitor(s).

15. A process according to claim 1, wherein the reaction is carried out in a reactor (R) in an alkyl (meth)acrylate (III)/amino alcohol (II) molar ratio of 1.7 to 2.2.

16. A process according to claim 1, wherein the catalyst is used in a proportion of $1 \times 10^{-3}$ to $8 \times 10^{-3}$ mol per mole of amino alcohol (II).

* * * * *

UNITED STATES PATENT AND TRADEMARK OFFICE
CERTIFICATE OF CORRECTION

PATENT NO.    : 6,437,173 B1
DATED         : August 20, 2002
INVENTOR(S)   : Hurtel et al.

It is certified that error appears in the above-identified patent and that said Letters Patent is hereby corrected as shown below:

Column 6,
Lines 25-29, delete in its entirety.

Signed and Sealed this

Twenty-first Day of January, 2003

JAMES E. ROGAN
*Director of the United States Patent and Trademark Office*